US012178899B2

(12) United States Patent
Nicou et al.

(10) Patent No.: US 12,178,899 B2
(45) Date of Patent: Dec. 31, 2024

(54) COMPOSITION COMPRISING THE COMBINATION OF TWO PARTICULAR OXIDATION DYE PRECURSORS AND AN ALKYL(POLY)GLYCOSIDE

(71) Applicant: L'Oreal, Paris (FR)

(72) Inventors: Valérie Nicou, Saint-Ouen (FR); Laurence Cottard-Mei, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 18/266,725

(22) PCT Filed: Dec. 16, 2021

(86) PCT No.: PCT/EP2021/086258
§ 371 (c)(1),
(2) Date: Jun. 12, 2023

(87) PCT Pub. No.: WO2022/129372
PCT Pub. Date: Jun. 23, 2022

(65) Prior Publication Data
US 2024/0050349 A1 Feb. 15, 2024

(30) Foreign Application Priority Data
Dec. 17, 2020 (FR) ........................... 2013464

(51) Int. Cl.
*A61Q 5/10* (2006.01)
*A61K 8/22* (2006.01)
*A61K 8/41* (2006.01)
*A61K 8/49* (2006.01)
*A61K 8/60* (2006.01)
*A61K 8/92* (2006.01)

(52) U.S. Cl.
CPC .............. *A61K 8/4973* (2013.01); *A61K 8/22* (2013.01); *A61K 8/411* (2013.01); *A61K 8/413* (2013.01); *A61K 8/415* (2013.01); *A61K 8/4926* (2013.01); *A61K 8/604* (2013.01); *A61K 8/922* (2013.01); *A61Q 5/10* (2013.01); *A61K 2800/882* (2013.01)

(58) Field of Classification Search
CPC ........ A61K 8/4973; A61K 8/22; A61K 8/411; A61K 8/413; A61K 8/415; A61K 8/4926; A61K 8/604; A61K 8/922; A61K 2800/882; A61Q 5/10
USPC ........................................................ 8/405
See application file for complete search history.

(56) References Cited

U.S. PATENT DOCUMENTS

| 3,589,978 | A | 6/1971 | Kamal et al. |
| 4,003,699 | A | 1/1977 | Rose et al. |
| 4,013,307 | A | 3/1977 | Dowd et al. |
| 4,137,180 | A | 1/1979 | Naik et al. |
| RE30,199 | E | 1/1980 | Rose et al. |
| 4,823,985 | A | 4/1989 | Grollier et al. |
| 4,874,554 | A | 10/1989 | Lange et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,766,576 | A | 6/1998 | Löwe et al. |
| 6,099,592 | A | 8/2000 | Vidal et al. |
| 6,284,003 | B1 | 9/2001 | Rose et al. |
| 6,730,789 | B1 | 5/2004 | Birault et al. |
| 8,608,810 | B2 * | 12/2013 | Sutton ................. A61K 8/411 8/408 |
| 8,663,341 | B2 * | 3/2014 | Sutton ................. A61K 8/66 8/408 |
| 9,918,919 | B1 | 3/2018 | Murphy et al. |
| 11,213,471 | B2 | 1/2022 | Nicou et al. |
| 11,324,682 | B2 | 5/2022 | Nicou et al. |
| 2007/0017040 | A1 | 1/2007 | Pasquier et al. |
| 2010/0275388 | A1 | 11/2010 | Audousset et al. |
| 2013/0340789 | A1 | 12/2013 | Sutton et al. |
| 2014/0053345 | A1 | 2/2014 | Rapold et al. |
| 2016/0271040 | A1 | 9/2016 | Zhang et al. |
| 2016/0271041 | A1 | 9/2016 | Zhang et al. |
| 2017/0165174 | A1 * | 6/2017 | Flohr ................. A61K 8/347 |
| 2018/0078478 | A1 | 3/2018 | Murphy et al. |
| 2018/0369104 | A1 | 12/2018 | Nicou et al. |
| 2020/0163851 | A1 | 5/2020 | Nicou et al. |
| 2020/0344560 | A1 | 10/2020 | Oplinger et al. |
| 2020/0345604 | A1 * | 11/2020 | Nicou ................. A61K 8/31 |

FOREIGN PATENT DOCUMENTS

| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0317542 A2 | 5/1989 |
| EP | 0399133 A1 | 11/1990 |
| EP | 0509382 A2 | 10/1992 |
| EP | 0516102 A1 | 12/1992 |
| EP | 0770375 A1 | 5/1997 |
| EP | 3777822 A1 | 2/2021 |
| FR | 2586913 A1 | 3/1987 |
| FR | 2733749 A1 | 11/1996 |

(Continued)

OTHER PUBLICATIONS

International Search Report and Written Opinion for counterpart Application No. PCT/EP2021/086254, dated Apr. 11, 2022.

(Continued)

*Primary Examiner* — Eisa B Elhilo

(74) *Attorney, Agent, or Firm* — THE MARBURY LAW GROUP, PLLC

(57) ABSTRACT

The invention relates to a composition comprising at least one oxidation coupler chosen from hydroxyethyl-3,4-methylenedioxyaniline of formula (I), one of its addition salts, its solvates and/or the solvates of its salts, at least one oxidation coupler chosen from 2-amino-5-ethylphenol of formula (II), one of its addition salts, its solvates and/or the solvates of its salts, and at least one alkyl(poly)glycoside. The invention also relates to a process for dyeing keratin fibres, preferably the hair, comprising the application of the composition to said keratin fibres.

20 Claims, No Drawings

(56) References Cited

FOREIGN PATENT DOCUMENTS

| | | |
|---|---|---|
| FR | 2801308 A1 | 5/2001 |
| FR | 2886136 A2 | 12/2006 |
| FR | 3045379 A1 | 6/2017 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 96/15765 A1 | 5/1996 |
| WO | 2013144260 A2 | 10/2013 |
| WO | 2016146813 A1 | 9/2016 |
| WO | 2018053177 A1 | 3/2018 |
| WO | 2022/129369 A1 | 6/2022 |
| WO | 2022/129373 A1 | 6/2022 |

OTHER PUBLICATIONS

International Search Report and Written Opinion for counterpart Application No. PCT/EP2021/086258, dated Apr. 21, 2022.
International Search Report and Written Opinion for counterpart Application No. PCT/EP2021/086259, dated Apr. 7, 2022.
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
Non-Final Office Action in U.S. Appl. No. 18/255,327, mailed Aug. 22, 2024, 11 pages.
Notice of Allowance in U.S. Appl. No. 18/255,337, mailed Aug. 28, 2024, 9 pages.

* cited by examiner

COMPOSITION COMPRISING THE COMBINATION OF TWO PARTICULAR OXIDATION DYE PRECURSORS AND AN ALKYL(POLY)GLYCOSIDE

CROSS REFERENCE TO RELATED APPLICATIONS

This is a National Stage Application of PCT/EP2021/086258, filed internationally on Dec. 16, 2021, which claims priority to French Application No. 2013464, filed Dec. 17, 2020, both of which are incorporated by reference herein in their entireties.

The invention relates to a composition comprising the combination of two particular oxidation dye precursors and an alkyl(poly)glycoside.

The invention also relates to a process for dyeing keratin fibres, in particular human keratin fibres such as hair, using this composition.

Finally, the invention relates to the use of such a composition for dyeing keratin fibres, and in particular human keratin fibres such as hair.

Many people have sought for a long time to modify the colour of their hair, and in particular to mask their grey hair.

It is known practice to dye keratin fibres, in particular human keratin fibres such as the hair, to obtain permanent colourings with dyeing compositions containing oxidation dye precursors, in particular oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds which, when combined with oxidizing products, can give rise to coloured compounds via a process of oxidative condensation.

It is also possible to vary the shades obtained with these oxidation bases by combining them with couplers or colour modifiers. The variety of molecules used as oxidation bases and couplers allows a wide range of colours to be obtained. However, the use of these dyeing compositions may have a certain number of drawbacks.

Specifically, after application to the keratin fibres, the dyeing power obtained may not be entirely satisfactory, or may even be weak, and lead to a restricted range of colours.

The colourings may also be insufficiently persistent with respect to external agents such as light, shampoo or perspiration, and may also be too selective, i.e. the difference in colouring is too great along the same keratin fibre that is differently sensitized between its end and its root.

There is a real need to provide a composition for dyeing keratin fibres, in particular human keratin fibres such as the hair, which does not have the drawbacks mentioned above, i.e. which is capable of resulting in a colouring having an intense colour, with an improved fastness and also good coverage of the grey hair and good selectivity, and which is capable of resulting in good dyeing performance levels, even after a period of storage.

These aims and others are achieved by the present invention, one subject of which is thus a composition, in particular for dyeing keratin fibres, comprising:

at least one oxidation coupler chosen from hydroxyethyl-3,4-methylenedioxyaniline of formula (I), one of its addition salts, its solvates and/or the solvates of its salts,

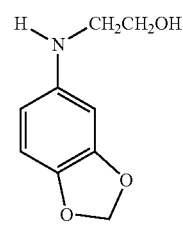

at least one oxidation coupler chosen from 2-amino-5-ethylphenol of formula (II), one of its addition salts, its solvates and/or the solvates of its salts,

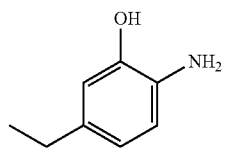

at least one alkyl(poly)glycoside.

Another subject of the present invention is a process for dyeing keratin fibres in which the composition according to the invention is applied to said fibres.

According to a preferred embodiment, the composition according to the invention is a composition for dyeing keratin fibres, in particular the hair.

The composition according to the invention may especially lead to chromatic, powerful, intense and sparingly selective colourings, i.e. to colourings that are uniform along the length of the fibre. It also allows various shades to be achieved in a very wide range of colours. Furthermore, it enables a good colour build-up.

This composition also gives particularly good coverage of depigmented keratin fibres, such as grey hair.

A subject of the invention is also a kit comprising, in a first compartment, a composition as defined above and, in a second compartment, an oxidizing composition comprising at least one chemical oxidizing agent.

According to the invention, the term "chemical oxidizing agent" is intended to mean an oxidizing agent other than atmospheric oxygen.

Other subjects, characteristics, aspects and advantages of the invention will become even more clearly apparent on reading the description and the examples which follow.

In that which follows, and unless otherwise indicated, the limits of a range of values are included in this range, in particular in the expressions "of between" and "ranging from . . . to . . . ".

Moreover, the expression "at least one" used in the present description is equivalent to the expression "one or more".

The composition according to the invention comprises at least two oxidation dye precursors.

Oxidation Couplers

The composition according to the invention comprises at least two particular oxidation couplers.

The composition according to the present invention comprises at least one coupler chosen from hydroxyethyl-3,4-methylenedioxyaniline of formula (I), one of its addition salts, its solvates and/or the solvates of its salts:

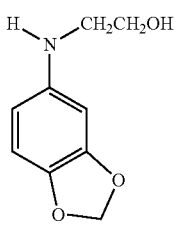

(I)

The addition salts of the compounds of formula (I) are chosen especially from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, aqueous ammonia, amines or alkanolamines.

Moreover, the solvates of the compounds of formula (I) more particularly represent the hydrates of these compounds and/or the combination of these compounds with a linear or branched $C_1$ to $C_4$ alcohol such as methanol, ethanol, isopropanol or n-propanol. Preferably, the solvates are hydrates.

The total content of coupler(s) chosen from hydroxyethyl-3,4-methylenedioxyaniline of formula (I), one of its addition salts, its solvates and/or the solvates of its salts preferably ranges from 0.001% to 20% by weight, more preferably from 0.005% to 15% by weight, more preferentially from 0.01% to 10% by weight, better still from 0.05% to 5%, even better still from 0.1% to 3% by weight, relative to the total weight of the composition.

The composition according to the present invention comprises at least one coupler chosen from 2-amino-5-ethylphenol of formula (II), one of its addition salts, its solvates and/or the solvates of its salts:

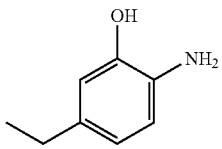

(II)

The addition salts of the compounds of formula (II) are chosen especially from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, aqueous ammonia, amines or alkanolamines.

Moreover, the solvates of the compounds of formula (II) more particularly represent the hydrates of these compounds and/or the combination of these compounds with a linear or branched $C_1$ to $C_4$ alcohol such as methanol, ethanol, isopropanol or n-propanol. Preferably, the solvates are hydrates.

The total content of coupler(s) chosen from 2-amino-5-ethylphenol of formula (11), one of its addition salts, its solvates and/or the solvates of its salts preferably ranges from 0.001% to 20% by weight, more preferably from 0.005% to 15% by weight, more preferentially from 0.01% to 10% by weight, better still from 0.05% to 5%, even better still from 0.1% to 3% by weight, relative to the total weight of the composition.

The total content of coupler(s) chosen from hydroxyethyl-3,4-methylenedioxyaniline of formula (I), 2-amino-5-ethylphenol of formula (II), one of their addition salts, their solvates and/or the solvates of their salts preferably ranges from 0.001% to 20% by weight, more preferably from 0.005% to 15% by weight, more preferentially from 0.01% to 10% by weight, better still from 0.05% to 5%, even better still from 0.1% to 3% by weight, relative to the total weight of the composition.

The composition according to the invention may optionally also comprise one or more additional couplers different from the compounds of formulae (I) and (II) and from their additional salts, their solvates and/or the solvates of their salts, advantageously chosen from those conventionally used in the dyeing of keratin fibres.

Among the additional couplers, mention may be made in particular of meta-phenylenediamines, meta-aminophenols, meta-diphenols, naphthalene-based coupling agents and heterocyclic coupling agents other than hydroxyethyl-3,4-methylenedioxyaniline, and also the corresponding addition salts.

Mention may be made, for example, of 6-hydroxybenzomorpholine, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, α-naphthol, 2-methyl-1-naphthol, 6-hydroxyindole, 4-hydroxyindole, 4-hydroxy-N-methylindole, 2-amino-3-hydroxypyridine, 3,5-diamino-2,6-dimethoxypyridine, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b][1,2,4]triazole, 2,6-dimethyl[3,2-c][1,2,4]triazole and 6-methylpyrazolo[1,5-a]benzimidazole, 2-methyl-5-aminophenol, 5-N-(β-hydroxyethyl)amino-2-methylphenol, 3-aminophenol and 3-amino-2-chloro-6-methylphenol, the corresponding addition salts with an acid and the corresponding mixtures.

In a particular embodiment, the composition according to the invention is free from oxidation couplers chosen from resorcinol, 2-methylresorcinol, 4-chlororesorcinol, their addition salts, their solvates and the solvates of their salts.

In general, the addition salts of the couplers that may be used in the context of the invention are chosen in particular from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, aqueous ammonia, amines or alkanolamines.

When the composition comprises one or more additional oxidation couplers, the total content of the additional coupler(s) different from the couplers of formulae (I) and (II), from their salts, from their solvates and from the solvates of their salts that is (are) present in the composition according to the invention preferably ranges from 0.001% to 20% by weight, more preferably from 0.005% to 15% by weight, more preferentially from 0.01% to 10% by weight, better still from 0.05% to 5%, even better still from 0.1% to 3% by weight, relative to the total weight of the composition.

Oxidation Bases

The composition according to the invention may also comprise at least one oxidation base.

Preferably, the composition according to the invention comprises at least one oxidation base.

By way of example, the oxidation bases are chosen from para-phenylenediamines, bis(phenyl)alkylenediamines, para-aminophenols, ortho-aminophenols, heterocyclic bases and the corresponding addition salts, the solvates and solvates of their salts.

Among the para-phenylenediamines that may be mentioned are, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-γ-hydroxypropyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the corresponding addition salts with an acid, the solvates and solvates of their salts.

Among the para-phenylenediamines mentioned above, particular preference is given to para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2-methoxymethyl-para-phenylenediamine, 2-γ-hydroxypropyl-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the corresponding addition salts with an acid, the solvates and solvates of their salts.

Among the bis(phenyl)alkylenediamines that may be mentioned are, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β3-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the corresponding addition salts, the solvates and solvates of their salts.

Among the para-aminophenols that are mentioned are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(3-hydroxyethylaminomethyl)phenol and 4-amino-2-fluorophenol, and the corresponding addition salts with an acid, the solvates and solvates of their salts.

Among the ortho-aminophenols that may be mentioned are, for example, 2-aminophenol, 2-amino-5-methylphenol, 2-amino-6-methylphenol and 5-acetamido-2-aminophenol, and the corresponding addition salts, the solvates and the solvates of their salts.

Among the heterocyclic bases that may be mentioned are, for example, pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts, the solvates and solvates of their salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts, the solvates and solvates of their salts.

More particularly, the oxidation bases that are useful in the present invention are chosen from 3-aminopyrazolo[1,5-a]pyridines and preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups, such as a di($C_1$-$C_4$)alkylpiperazinium group; or c) a ($C_1$-$C_6$)alkoxy group optionally substituted with one or more hydroxyl groups, such as a β-hydroxyalkoxy group, and the corresponding addition salts, the solvates and solvates of their salts.

Among the pyrimidine derivatives which may be mentioned are the compounds described, for example, in patents DE 2359399, JP 88-169571, JP 05-63124 and EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the corresponding addition salts, the solvates and solvates of their salts. Use may also be made of 4,5-diamino-1-(3-methoxyethyl)pyrazole.

A 4,5-diaminopyrazole will preferably be used and even more preferentially 4,5-diamino-1-(β-hydroxyethyl)pyrazole and/or a corresponding salt, the solvates and solvates of their salts.

The pyrazole derivatives which may also be mentioned comprise diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt, the solvates and solvates of their salts.

Use will preferably be made, as heterocyclic bases, of 4,5-diamino-1-(pi-hydroxyethyl)pyrazole and/or 2,3-diamino-6,7-dihydro-1H,5H-pyrazolo[1,2-a]pyrazol-1-one and/or 2-β-hydroxyethoxy-3-aminopyrazolo[1,5-a]pyridine and/or a corresponding salt.

These compounds may also be present in the form of solvates.

The addition salts of the oxidation bases which can be present in the composition according to the invention are chosen especially from the addition salts with an acid, such as the hydrochlorides, hydrobromides, sulfates, citrates, succinates, tartrates, lactates, tosylates, benzenesulfonates, methanesulfonates, phosphates and acetates, and the addition salts with a base, such as sodium hydroxide, potassium hydroxide, aqueous ammonia, amines or alkanolamines.

Moreover, the solvates of the additional oxidation bases more particularly represent the hydrates of said oxidation bases and/or the combination of said oxidation bases with a linear or branched $C_1$ to $C_4$ alcohol such as methanol, ethanol, isopropanol or n-propanol. Preferably, the solvates are hydrates.

Preferably, the oxidation base(s) is (are) chosen from para-phenylenediamines, bis(phenyl)alkylenediamines, para-aminophenols, ortho-aminophenols, heterocyclic bases, and the corresponding addition salts, and mixtures thereof; more preferentially from 2-methoxymethyl-para-phenylenediamine, 2-β-hydroxyethyl-para-phenylenediamine, 2-γ-hydroxypropyl-para-phenylenediamine, their addition salts, their solvates, the solvates of their salts and mixtures thereof.

In a particular embodiment, the composition according to the invention is free from oxidation bases chosen from para-phenylenediamine, para-toluenediamine, their addition salts, their solvates and the solvates of their salts.

When it (they) is (are) present, the oxidation base(s) is (are) present in a content ranging from 0.001% to 20% by weight, more preferably from 0.005% to 15% by weight, more preferentially from 0.01% to 10% by weight, better still from 0.05% to 5%, even better still from 0.1% to 3% by weight, relative to the weight of the composition.

According to a preferred embodiment, the oxidation base(s) chosen from 2-methoxymethyl-para-phenylenediamine, 2-β-hydroxyethyl-para-phenylenediamine, 2-γ-hydroxypropyl-para-phenylenediamine, their addition salts, and mixtures thereof is (are) present in a content ranging from 0.001% to 20% by weight, more preferably from 0.005% to 15% by weight, more preferentially from 0.01% to 10% by weight, better still from 0.05% to 5%, even better still from 0.1% to 3% by weight, relative to the weight of the composition.

Advantageously, the weight ratio between the total content of the oxidation base(s) and the total content of coupler chosen from hydroxyethyl-3,4-methylenedioxyaniline of formula (I), 2-amino-5-ethylphenol of formula (II), one of their addition salts, their solvates and/or the solvates of their salts is between 0.1 and 10, preferably between 0.5 and 5.

Advantageously, the weight ratio between the total content of the oxidation base(s) and the total content of the couplers is between 0.1 and 10, preferably between 0.3 and 3.

Alkyl(poly)glycoside

The composition according to the invention further comprises one or more alkyl(poly)glycoside(s).

The alkyl(poly)glycoside(s) may be represented by the following general formula: $R_1O-(R_2O)t-(G)v$ in which:

$R_1$ represents a linear or branched alkyl or alkenyl radical comprising 6 to 24 carbon atoms and especially 8 to 18 carbon atoms, or an alkylphenyl radical of which the linear or branched alkyl radical comprises 6 to 24 carbon atoms and especially 8 to 18 carbon atoms;

$R_2$ represents an alkylene radical comprising from 2 to 4 carbon atoms,

G represents a sugar unit comprising from 5 to 6 carbon atoms, t denotes a value ranging from 0 to 10, preferably from 0 to 4, v denotes a value ranging from 1 to 15, preferably from 1 to 4.

Preferably, the alkyl(poly)glycosides are compounds of the formula described above in which:

$R_1$ denotes a saturated or unsaturated and linear or branched alkyl radical comprising from 8 to 18 carbon atoms $R_2$ represents an alkylene radical comprising from 2 to 4 carbon atoms, t denotes a value ranging from 0 to 3, preferably equal to 0, G denotes glucose, fructose or galactose, preferably glucose;

the degree of polymerization, that is to say the value of v, being able to range from 1 to 15, preferably from 1 to 4; the mean degree of polymerization more particularly being of between 1 and 2.

The glucoside bonds between the sugar units are generally of 1-6 or 1-4 type, preferably of 1-4 type. Preferably, the alkyl(poly)glycoside surfactant is an alkyl(poly)glucoside surfactant. C8/C16 alkyl (poly)glucosides of 1-4 type, and in particular decyl glucosides and caprylyl/capryl glucosides, are very particularly preferred.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or else the products sold by the company Chem Y under the name AG10 LK.

Preferably, use is made of C8/C10 alkyl (poly)glycosides, in particular as an aqueous 60% solution, such as those sold by SEPPIC under the reference Oramix CG 110.

Preferentially, the composition comprises one or more alkyl(poly)glycosides chosen from, alone or as a mixture, (C6-C24 alkyl)(poly)glycosides, and more particularly (C8-C18 alkyl)(poly)glycosides, preferably chosen from coco glucoside, lauryl glucoside, caprylyl/capryl glucoside.

Preferably, the composition according to the invention comprises the alkyl(poly)glycoside(s) in a content ranging from 0.05% to 20% by weight, preferably from 0.1% to 15% by weight, better still from 0.5% to 10% by weight, even better still from 1% to 5%, relative to the total weight of the composition according to the invention.

Fatty Substances

The composition according to the invention may comprise one or more fatty substances.

The term "fatty substance" is understood to mean an organic compound that is insoluble in water at 25° C. and at atmospheric pressure ($1.013 \times 10^5$ Pa) (solubility of less than 5% by weight, and preferably less than 1% by weight, even more preferentially less than 0.1% by weight). They bear in their structure at least one hydrocarbon-based chain including at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Advantageously, the fatty substances that may be used in the present invention are neither (poly)oxyalkylenated nor (poly)glycerolated.

Preferably, the fatty substances that are of use according to the invention are non-silicone.

The term "non-silicone fatty substance" is intended to mean a fatty substance not containing any Si-O bonds and the term "silicone fatty substance" is intended to mean a fatty substance containing at least one Si—O bond.

Useful fatty substances according to the invention may be liquid fatty substances (or oils) and/or solid fatty substances. A liquid fatty substance is understood to be a fatty substance having a melting point of less than or equal to 25° C. at atmospheric pressure ($1.013 \times 10^5$ Pa).

A solid fatty substance is understood to be a fatty substance having a melting point of greater than 25° C. at atmospheric pressure ($1.013 \times 10^5$ Pa).

For the purposes of the present invention, the melting point corresponds to the temperature of the most endothermic peak observed on thermal analysis (differential scanning calorimetry or DSC) as described in the standard ISO 11357-3; 1999. The melting point may be measured using a differential scanning calorimeter (DSC), for example the calorimeter sold under the name "MDSC 2920" by the company TA Instruments. In the present application, all the melting points are determined at atmospheric pressure ($1.013 \times 10^5$ Pa).

More particularly, the liquid fatty substance(s) according to the invention is (are) chosen from $C_6$ to $C_{16}$ liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid esters of fatty acid and/or of fatty alcohol other than triglycerides, and silicone oils, and mixtures thereof.

It is recalled that the fatty alcohols, esters and acids more particularly contain at least one saturated or unsaturated, linear or branched hydrocarbon-based group, comprising from 6 to 40 and better still from 8 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the $C_6$ to $C_{16}$ liquid hydrocarbons, the latter may be linear, branched, or optionally cyclic, and are preferably chosen from alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, of mineral or synthetic origin, and are preferably chosen from liquid paraffin or liquid petroleum jelly (INCI name mineral oil or paraffinum liquidum), polydecenes, hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid triglycerides of fatty acids comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stéarinerie Dubois or those sold under the names Miglyol® 810, 812 and 818 by the company Dynamit Nobel, jojoba oil and shea butter oil, and mixtures thereof.

As regards the fluoro oils, they may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or else bromoperfluorooctyl sold under the name Foralkyl® by the company Atochem; nonafluoromethoxybutane and nonafluoroethoxyisobutane; perfluoromorpholine derivatives, such as 4-trifluoromethylperfluoromorpholine sold under the name PF 5052® by the company 3M.

The liquid fatty alcohols that are suitable for use in the invention are more particularly chosen from linear or branched, saturated or unsaturated alcohols, preferably unsaturated or branched alcohols, comprising from 6 to 40 carbon atoms, preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or of fatty alcohols, other than the triglycerides mentioned previously, mention may be made especially of esters of saturated or unsaturated, linear C1 to C26 or branched C3 to C26 aliphatic mono- or polyacids and of saturated or unsaturated, linear C1 to C26 or branched C3 to C26 aliphatic mono- or polyalcohols, the total carbon number of the esters being greater than or equal to 6, more advantageously greater than or equal to 10.

Preferably, for the esters of monoalcohols, at least one from among the alcohol and the acid from which the esters of the invention are derived is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononanoate; octyldodecyl erucate; oleyl erucate; ethyl palmitate, isopropyl palmitate, such as 2-ethylhexyl palmitate, 2-octyldecyl palmitate; alkyl myristates such as isopropyl myristate; isobutyl stearate; 2-hexyldecyl laurate, and mixtures thereof.

Preferably, among the monoesters of monoacids and of monoalcohols, use will be made of ethyl palmitate and isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Still within the context of this variant, esters of C4 to $C_{22}$ dicarboxylic or tricarboxylic acids and of $C_1$ to $C_{22}$ alcohols and esters of mono-, di- or tricarboxylic acids and of $C_2$ to $C_{16}$ di-, tri-, tetra- or pentahydroxy alcohols may also be used.

Mention may especially be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; polyethylene glycol distearates, and mixtures thereof.

The composition may also comprise, as fatty ester, sugar esters and diesters of $C_6$ to $C_{30}$, preferably of $C_{12}$ to $C_{22}$, fatty acids. It is recalled that the term "sugar" refers to oxygen-bearing hydrocarbon-based compounds bearing several alcohol functions, with or without aldehyde or ketone functions, and which include at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described above and of linear or branched, saturated or unsaturated C6 to C30 and preferably C12 to C22 fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof, for instance especially the mixed oleopalmitate, oleostearate and palmitostearate esters.

More particularly, use is made of monoesters and diesters and especially sucrose, glucose or methylglucose mono- or dioleates, -stearates, -behenates, -oleopalmitates, -linoleates, -linolenates and -oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

The silicone oils that may be used in the composition according to the present invention may be volatile or non-volatile, cyclic, linear or branched silicone oils, which are unmodified or modified with organic groups, and preferably have a viscosity from $5 \times 10^{-6}$ to 2.5 m²/s at 25° C., and preferably $1 \times 10^{-5}$ to 1 m²/s.

Preferably, the silicone oils are chosen from polydialkylsiloxanes, especially polydimethylsiloxanes (PDMS), and liquid polyorganosiloxanes including at least one aryl group.

These silicone oils may also be organomodified. The organomodified silicone oils that may be used in accordance with the invention are preferably liquid silicones as defined above and including in their structure one or more organofunctional groups attached via a hydrocarbon-based group, chosen, for example, from amine groups and alkoxy groups.

Organopolysiloxanes are defined in greater detail in Walter Noll's "Chemistry and Technology of Silicones" (1968), Academic Press. They may be volatile or non-volatile.

When they are volatile, the silicone oils are more particularly chosen from those with a boiling point of between 60° C. and 260° C., and even more particularly from:
  (i) cyclic polydialkylsiloxanes including from 3 to 7 and preferably from 4 to 5 silicon atoms. These are, for example, octamethylcyclotetrasiloxane sold notably under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide.

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones falling within this category are also described in the article published in Cosmetics and Toiletries, Vol. 91, January 76, pp. 27-32, Todd & Byers, "Volatile Silicone Fluids for Cosmetics".

Non-volatile polydialkylsiloxanes are preferably used.

These silicone oils are more particularly chosen from polydialkylsiloxanes, among which mention may be made mainly of polydimethylsiloxanes bearing trimethylsilyl end groups.

The viscosity of the silicones is measured at 25° C. according to the standard ASTM 445, Appendix C.

Among these polydialkylsiloxanes, mention may be made, in a nonlimiting manner, of the following commercial products:

the Silbione® oils of the 47 and 70 047 series or the Mirasil® oils sold by Rhodia, such as, for example, the oil 70 047 V 500 000;

the oils of the Mirasil® series sold by the company Rhodia;

the oils of the 200 series from the company Dow Corning, such as DC200 having a viscosity of 60 000 mm²/s;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

The organomodified silicones that may be used in accordance with the invention are silicones as defined above and comprising in their structure one or more organofunctional groups attached via a hydrocarbon-based group.

As regards the liquid polyorganosiloxanes including at least one aryl group, they may especially be polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Among these polyalkylarylsiloxanes, examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, mention may be made of polyorganosiloxanes including:

substituted or unsubstituted amine groups, such as the products sold under the names GP 4 Silicone Fluid and GP 7100 by the company Genesee or the products sold under the names Q2 8220 and Dow Corning 929 or 939 by the company Dow Corning. The substituted amine groups are in particular C1 to C4 aminoalkyl groups;

alkoxy groups, hydroxyl groups.

The solid fatty substances according to the invention preferably have a viscosity of greater than 2 Pa·s, measured at 25° C. and at a shear rate of 1 s$^{-1}$.

The solid fatty substance(s) is (are) preferably chosen from solid fatty acids, solid fatty alcohols, solid esters of fatty acids and/or of fatty alcohols, waxes, ceramides and mixtures thereof.

The term "fatty acids" is intended to mean a long-chain carboxylic acid comprising from 6 to 40 carbon atoms, preferably from 8 to 30 carbon atoms. The solid fatty acids according to the invention preferentially comprise from 10 to 30 carbon atoms and better still from 14 to 22 carbon atoms. They may optionally be hydroxylated. These fatty acids are neither oxyalkylenated nor glycerolated.

The solid fatty acids that may be used in the present invention are chosen especially from myristic acid, cetylic acid (palmitic acid), arachidic acid, stearic acid, lauric acid, behenic acid, 12-hydroxystearic acid, and mixtures thereof.

Particularly preferably, the solid fatty acid(s) is (are) chosen from lauric acid, stearic acid, myristic acid, cetylic acid (palmitic acid), and mixtures thereof.

The term "fatty alcohol" is intended to mean a long-chain aliphatic alcohol comprising from 6 to 40 carbon atoms, preferably from 8 to 30 carbon atoms, and comprising at least one hydroxyl group OH. These fatty alcohols are neither oxyalkylenated nor glycerolated.

The solid fatty alcohols may be saturated or unsaturated, and linear or branched, and include from 8 to 40 carbon atoms, preferably from 10 to 30 carbon atoms. Preferably, the solid fatty alcohols have the structure R—OH with R denoting a linear alkyl group, optionally substituted with one or more hydroxyl groups, comprising from 8 to 40, preferentially from 10 to 30 carbon atoms, better still from 10 to 30, or even from 12 to 24 atoms, and even better still from 14 to 22 carbon atoms.

The solid fatty alcohols that may be used are preferably chosen from saturated or unsaturated, linear or branched, preferably linear and saturated, (mono)alcohols including from 8 to 40 carbon atoms, better still from 10 to 30, or even from 12 to 24 atoms, and even better still from 14 to 22 carbon atoms.

The solid fatty alcohols that may be used may be chosen, alone or as a mixture, from: myristyl alcohol (or 1-tetradecanol); cetyl alcohol (or 1-hexadecanol); stearyl alcohol (or 1-octadecanol); arachidyl alcohol (or 1-eicosanol); behenyl alcohol (or 1-docosanol); lignoceryl alcohol (or 1-tetracosanol); ceryl alcohol (or 1-hexacosanol); montanyl alcohol (or 1-octacosanol); myricyl alcohol (or 1-triacontanol).

Preferentially, the solid fatty alcohol is chosen from cetyl alcohol, stearyl alcohol, behenyl alcohol, myristyl alcohol, arachidyl alcohol, and mixtures thereof, such as cetylstearyl alcohol or cetearyl alcohol. Particularly preferably, the solid fatty alcohol is cetylstearyl or cetearyl alcohol.

The solid esters of a fatty acid and/or of a fatty alcohol that may be used are preferably chosen from esters resulting from a $C_9$-$C_{26}$ carboxylic fatty acid and/or from a $C_9$-$C_{26}$ fatty alcohol.

Preferably, these solid fatty esters are esters of a linear or branched, saturated carboxylic acid including at least 10 carbon atoms, preferably from 10 to 30 carbon atoms and more particularly from 12 to 24 carbon atoms, and of a linear or branched, saturated monoalcohol including at least 10 carbon atoms, preferably from 10 to 30 carbon atoms and more particularly from 12 to 24 carbon atoms. The saturated carboxylic acids may be optionally hydroxylated, and are preferably monocarboxylic acids.

Esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxylated alcohols may also be used.

Mention may especially be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from $C_9$-$C_{26}$ alkyl palmitates, notably myristyl palmitate, cetyl palmitate or stearyl palmitate; $C_9$-$C_{26}$ alkyl myristates, such as cetyl myristate, stearyl myristate and myristyl myristate; $C_9$-$C_{26}$ alkyl stearates, in particular myristyl stearate, cetyl stearate and stearyl stearate; and mixtures thereof.

For the purposes of the present invention, a wax is a lipophilic compound, which is solid at 25° C. and atmospheric pressure, with a reversible solid/liquid change of state, having a melting point greater than about 40° C. and which may range up to 200° C., and having in the solid state an anisotropic crystal organisation. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but on returning the temperature of the mixture to ambient temperature, recrystallization of the wax, which is microscopically and macroscopically detectable (opalescence), is obtained.

In particular, the waxes that are suitable for use in the invention may be chosen from waxes of animal, plant or mineral origin, non-silicone synthetic waxes, and mixtures thereof.

Mention may be made notably of hydrocarbon-based waxes, for instance beeswax, notably of biological origin, lanolin wax, and Chinese insect waxes; rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of $C_{20}$ to $C_{60}$ microcrystalline waxes, such as Microwax HW.

Mention may also be made of the MW 500 polyethylene wax sold under the reference Permalen 50-L polyethylene.

Mention may also be made of waxes obtained by catalytic hydrogenation of animal or plant oils containing linear or branched $C_8$ to $C_{32}$ fatty chains. Among these waxes, mention may notably be made of isomerized jojoba oil, such as the trans-isomerized partially hydrogenated jojoba oil, notably the product manufactured or sold by the company Desert Whale under the commercial reference Iso-Jojoba-50®, hydrogenated sunflower oil, hydrogenated castor oil, hydrogenated coconut oil, hydrogenated lanolin oil, and bis(1,1,1-trimethylolpropane) tetrastearate, notably the product sold under the name Hest 2T-4S® by the company Heterene.

The waxes obtained by hydrogenation of castor oil esterified with cetyl alcohol, such as those sold under the names Phytowax Castor 16L64® and 22L73® by the company Sophim, may also be used.

A wax that may also be used is a $C_{20}$ to $C_{40}$ alkyl (hydroxystearyloxy)stearate (the alkyl group comprising from 20 to 40 carbon atoms), alone or as a mixture. Such a wax is notably sold under the names "Kester Wax K 82 P®", "Hydroxypolyester K 82 P®" and "Kester Wax K 80 P®" by the company Koster Keunen.

It is also possible to use microwaxes in the compositions of the invention; mention may be made notably of carnauba microwaxes, such as the product sold under the name MicroCare 350® by the company Micro Powders, synthetic-wax microwaxes, such as the product sold under the name MicroEase 114S® by the company Micro Powders, microwaxes constituted of a mixture of carnauba wax and of polyethylene wax, such as the products sold under the names Micro Care 300® and 310® by the company Micro Powders, microwaxes constituted of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

The waxes are preferably chosen from mineral waxes, for instance paraffin, petroleum jelly, lignite or ozokerite wax; plant waxes, for instance cocoa butter or cork fibre or sugar cane waxes, olive tree wax, rice wax, hydrogenated jojoba wax, ouricury wax, carnauba wax, candelilla wax, esparto grass wax, or absolute waxes of flowers, such as the essential wax of blackcurrant blossom sold by the company Bertin (France); waxes of animal origin, for instance beeswaxes or modified beeswaxes (cera bellina), spermaceti, lanolin wax and lanolin derivatives; microcrystalline waxes; and mixtures thereof.

The ceramides, or ceramide analogues such as glycoceramides, that may be used in the compositions according to the invention are known; mention may in particular be made of ceramides of classes I, II, III and V according to the Dawning classification.

The ceramides or analogues thereof that may be used preferably correspond to the following formula: $R^3CH(OH)CH(CH_2OR^2)(NHCOR^1)$, in which:

$R^1$ denotes a linear or branched, saturated or unsaturated alkyl group, derived from $C_{14}$-$C_{30}$ fatty acids, it being possible for this group to be substituted with a hydroxyl group in the alpha position, or a hydroxyl group in the omega position esterified with a saturated or unsaturated $C_{16}$-$C_{30}$ fatty acid;

$R^2$ denotes a hydrogen atom, a (glycosyl)n group, a (galactosyl)m group or a sulfogalactosyl group, in which n is an integer ranging from 1 to 4 and m is an integer ranging from 1 to 8;

$R^3$ denotes a $C_{15}$-$C_{26}$ hydrocarbon-based group, saturated or unsaturated in the alpha position, it being possible for this group to be substituted with one or more $C_1$-$C_{14}$ alkyl groups; it being understood that in the case of natural ceramides or glycoceramides, $R^3$ may also denote a $C_{15}$-$C_{26}$ alpha-hydroxyalkyl group, the hydroxyl group being optionally esterified with a $C_{16}$-$C_{30}$ alpha-hydroxy acid.

The ceramides that are more particularly preferred are the compounds for which $R^1$ denotes a saturated or unsaturated alkyl derived from $C_{16}$-$C_{22}$ fatty acids; $R^2$ denotes a hydrogen atom and $R^3$ denotes a saturated linear $C_{15}$ group.

Preferentially, use is made of ceramides for which $R^1$ denotes a saturated or unsaturated alkyl group derived from $C_{14}$-$C_{30}$ fatty acids; $R^2$ denotes a galactosyl or sulfogalactosyl group; and $R^3$ denotes a —CH=CH-$(CH2)_{12}$-CH3 group.

Use may also be made of the compounds for which $R^1$ denotes a saturated or unsaturated alkyl radical derived from $C_{12}$-$C_{22}$ fatty acids; $R^2$ denotes a galactosyl or sulfogalactosyl radical and $R^3$ denotes a saturated or unsaturated $C_{12}$-$C_{22}$ hydrocarbon-based radical and preferably a —CH=CH-$(CH2)_{12}$-CH3 group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypalmitoyl]aminooctadecane-1,3-diol; 2-N-stearoylaminooctadecane-1,3,4-triol and in particular N-stearoylphytosphingosine, 2-N-palmitoylaminohexadecane-1,3-diol, N-linoleoyldihydrosphingosine, N-oleoyldihydrosphingosine, N-palmitoyldihydrosphingosine, N-stearoyldihydrosphingosine, and N-behenoyldihydrosphingosine, N-docosanoyl-N-methyl-D-glucamine, cetylic acid N-(2-hydroxyethyl)-N-(3-cetyloxy-2-hydroxypropyl)amide and bis (N-hydroxyethyl-N-cetyl)malonamide; and mixtures thereof. N-Oleoyldihydrosphingosine will preferably be used.

The solid fatty substances are preferably chosen from solid fatty acids, solid fatty alcohols, and mixtures thereof.

According to a preferred embodiment, the composition according to the invention comprises at least one liquid fatty substance, preferentially chosen from liquid hydrocarbons containing more than 16 carbon atoms, plant oils, liquid fatty alcohols and liquid fatty esters, silicone oils and mixtures thereof.

Preferentially, the liquid fatty substance(s) is (are) chosen from liquid hydrocarbons comprising more than 16 carbon atoms, in particular liquid petroleum jelly, liquid fatty alcohols, and mixtures thereof.

According to another preferred embodiment, the composition according to the invention comprises at least one solid fatty substance, preferentially chosen from solid fatty alcohols.

According to another preferred embodiment, the composition according to the invention comprises at least one liquid fatty substance and at least one solid fatty substance, preferentially at least one liquid fatty alcohol and at least one solid fatty alcohol.

When the composition according to the invention comprises one or more fatty substances, the total content of the fatty substance(s) preferably ranges from 5% to 80% by weight, more preferentially from 8% to 70% by weight, and better still from 10% to 65% by weight, relative to the total weight of the composition.

In one particular embodiment, the composition according to the invention comprises one or more fatty substances, the total content of the fatty substance(s) preferably ranging from 30% to 80% by weight, more preferentially from 35% to 70% by weight, and better still from 40% to 65% by weight, relative to the total weight of the composition.

In another particular embodiment, the composition according to the invention comprises one or more liquid fatty substances, the total content of the liquid fatty substance(s) preferably ranging from 30% to 80% by weight, more preferentially from 35% to 70% by weight, and better still from 40% to 65% by weight, relative to the total weight of the composition.

Surfactants

The composition according to the present invention can comprise one or more surfactants different from the alkyl (poly)glycosides. These may be chosen preferably from anionic surfactants, non-ionic surfactants, cationic surfactants and/or mixtures thereof.

The term "anionic surfactant" is understood to mean a surfactant including, as ionic or ionizable groups, only anionic groups. These anionic groups are preferably chosen from the following groups: $CO_2H$, $CO_2$-, $SO_3H$, $SO_3$-, $OSO_3H$, $OSO_3$-, $H_2PO_3$-, $HPO_3$-, $PO_3^{2-}$, $H_2PO_2$, $HPO_2$-, $PO_2^{2-}$, POH and PO-.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N—($C_1$-$C_4$)alkyl N-acyltaurates, salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds (unless specified otherwise) generally comprising from 6 to 24 carbon atoms and the aryl group generally denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from C6-$C_{24}$ alkyl polyglycoside-citrates, C6-$C_{24}$ alkyl polyglycoside-tartrates and $C_6$-$C_{24}$ alkyl polyglycoside-sulfosuccinates.

When the anionic surfactant(s) is (are) in salt form, they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may notably be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

The anionic surfactants optionally present may be mild anionic surfactants, i.e. anionic surfactants without a sulfate function.

As regards mild anionic surfactants, mention may be made in particular of the following compounds and salts thereof, and also mixtures thereof: polyoxyalkylenated alkyl ether carboxylic acids; polyoxyalkylenated alkylaryl ether carboxylic acids; polyoxyalkylenated alkylamido ether carboxylic acids, in particular those comprising 2 to 50 ethylene oxide groups; alkyl D-galactoside uronic acids; acyl sarcosinates; acyl glutamates; and alkylpolyglycoside carboxylic esters.

Use may be made most particularly of polyoxyalkylenated alkyl ether carboxylic acids, for instance lauryl ether carboxylic acid (4.5 OE), sold, for example, under the name Akypo RLM 45 CA from Kao.

Among the anionic surfactants mentioned above, use is preferably made of the sulfated surfactants such as the alkyl sulfates or alkyl ether sulfates, and the acyl glutamates, more preferentially the alkyl sulfates.

The non-ionic surfactant(s) that may be used in the composition of the present invention are in particular described, for example, in the *Handbook of Surfactants* by M. R. Porter, published by Blackie & Son (Glasgow and London), 1991, pages 116-178.

As examples of non-ionic surfactants different from the alkyl(poly)glycosides, mention may be made of the following compounds, alone or as a mixture:

oxyalkylenated ($C_8$-$C_{24}$)alkylphenols;
saturated or unsaturated, linear or branched, oxyalkylenated or glycerolated $C_8$-$C_{40}$ alcohols, preferably comprising one or two fatty chains;
saturated or unsaturated, linear or branched, oxyalkylenated $C_8$ to $C_{30}$ fatty acid amides;
esters of saturated or unsaturated, linear or branched, $C_8$ to $C_{30}$ acids and of polyethylene glycols;
esters of saturated or unsaturated, linear or branched, $C_8$ to $C_{30}$ acids and of sorbitol which are preferably oxyethylenated;
fatty acid esters of sucrose;
oxyethylenated or non-oxyethylenated $C_8$-$C_{30}$ fatty acid esters of sorbitan;
saturated or unsaturated oxyethylenated plant oils;
condensates of ethylene oxide and/or of propylene oxide;
N-($C_8$-$C_{30}$)alkylglucamine and N—($C_8$-$C_{30}$)acylmethylglucamine derivatives;
amine oxides.

They are notably chosen from alcohols, α-diols and ($C_1$-$C_{20}$)alkylphenols, these compounds being ethoxylated, propoxylated or glycerolated, and bearing at least one fatty chain comprising, for example, from 8 to 24 carbon atoms, preferably from 8 to 18 carbon atoms, the number of ethylene oxide or propylene oxide groups possibly ranging notably from 1 to 200, and the number of glycerol groups possibly ranging notably from 1 to 30.

Mention may also be made of condensates of ethylene oxide and of propylene oxide with fatty alcohols; ethoxylated fatty amides preferably having from 1 to 30 ethylene oxide units, polyglycerolated fatty amides comprising on average 1 to 5, and in particular 1.5 to 4, glycerol groups, ethoxylated fatty acid esters of sorbitan having from 1 to 30 ethylene oxide units, fatty acid esters of sucrose, fatty acid esters of polyethylene glycol, oxyethylenated plant oils, N—($C_6$-$C_{24}$ alkyl)glucamine derivatives, amine oxides such as ($C_{10}$-$C_{14}$)alkylamine oxides or N—($C_{10}$-$C_{14}$ acyl)aminopropylmorpholine oxides.

The $C_8$-$C_{30}$ and preferably $C_{12}$-$C_{22}$ fatty acid esters (especially monoesters, diesters and triesters) of sorbitan may be chosen from:

sorbitan caprylate; sorbitan cocoate; sorbitan isostearate; sorbitan laurate; sorbitan oleate; sorbitan palmitate; sorbitan stearate; sorbitan diisostearate; sorbitan dioleate; sorbitan distearate; sorbitan sesquicaprylate; sorbitan sesquiisostearate; sorbitan sesquioleate; sorbitan sesquistearate; sorbitan triisostearate; sorbitan trioleate; and sorbitan tristearate.

The polyoxyethylenated $C_8$-$C_{30}$ (preferably $C_{12}$-$C_{18}$) fatty acid esters (especially monoesters, diesters and triesters) of sorbitan, especially containing from 2 to 20 mol of ethylene oxide, may be chosen from polyoxyethylenated esters, especially containing from 2 to 30 mol of ethylene oxide, of $C_{12}$-$C_{18}$ fatty acids, in particular lauric, myristic, cetylic or stearic acid, and of sorbitan, such as:

polyoxyethylenated sorbitan monolaurate (4 OE) (Polysorbate-21), polyoxyethylenated sorbitan monolaurate (20 OE) (Polysorbate-20), polyoxyethylenated sorbitan monopalmitate (20 OE) (Polysorbate-40), polyoxyethylenated sorbitan monostearate (20 OE) (Polysorbate-60), polyoxyethylenated sorbitan monostearate (4 OE) (Polysorbate-61), polyoxyethylenated sorbitan monooleate (20 OE) (Polysorbate-80), polyoxyethylenated sorbitan monooleate (5 OE) (Polysorbate-81), polyoxyethylenated sorbitan tristearate (20 OE) (Polysorbate-65), polyoxyethylenated sorbitan trioleate (20 OE) (Polysorbate-85).

The polyoxyethylenated $C_8$-$C_{30}$ (preferably $C_{12}$-$C_{18}$) fatty acid esters (especially monoesters, diesters, triesters and tetraesters) of sorbitan, especially containing from 2 to 20 mol of ethylene oxide, may be chosen from polyoxyethylenated esters, especially containing from 2 to 20 mol of ethylene oxide, such as: of $C_{12}$-$C_{18}$ fatty acids, in particular lauric, myristic, cetylic or stearic acid, and of sorbitan, such as:

the ester polyoxyethylenated with 20 OE of sorbitan and of cocoic acid (PEG-20 sorbitan cocoate)
the polyoxyethylenated esters (especially containing from 2 to 20 OE) of sorbitan and of isostearic acid (such as PEG-2 sorbitan isostearate; PEG-5 sorbitan isostearate; PEG-20 sorbitan isostearate such as the product sold under the name Nikkol TI 10 V by the company Nikkol),
the polyoxyethylenated esters (especially containing from 2 to 20 OE) of sorbitan and of lauric acid (such as PEG-10 sorbitan laurate),
the polyoxyethylenated esters (especially containing from 2 to 20 OE) of sorbitan and of oleic acid containing 10 oxyethylene groups (such as PEG-6 sorbitan oleate; PEG-20 sorbitan oleate),
the polyoxyethylenated esters (in particular containing from 3 to 20 OE) of sorbitan and of stearic acid (such as PEG-3 sorbitan stearate; PEG-4 sorbitan stearate; PEG-6 sorbitan stearate).

The non-ionic surfactant(s) is (are) preferably chosen from ethoxylated $C_8$-$C_{24}$ fatty alcohols comprising from 1 to 200 ethylene oxide groups, ethoxylated $C_8$-$C_{30}$ fatty acid esters of sorbitan having from 1 to 30 ethylene oxide units, and mixtures thereof.

The cationic surfactant(s) that may be used in the composition according to the invention is (are) generally chosen from optionally polyoxyalkylenated primary, secondary or tertiary fatty amines, quaternary ammonium salts, and mixtures thereof.

The fatty amines generally comprise at least one $C_8$-$C_{30}$ hydrocarbon-based chain. Among the fatty amines that may be used according to the invention, examples that may be mentioned include stearylamidopropyldimethylamine and distearylamine.

Examples of quaternary ammonium salts that may notably be mentioned include:

those corresponding to the general formula (X) below:

in which the groups $R_8$ to $R_{11}$, which may be identical or different, represent a linear or branched aliphatic group comprising from 1 to 30 carbon atoms, or an aromatic group such as aryl or alkylaryl, at least one of the groups $R_8$ to $R_{11}$ comprising from 8 to 30 carbon atoms and preferably from 12 to 24 carbon atoms. The aliphatic groups may include heteroatoms such as especially oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates and ($C_1$-$C_4$)alkylsulfonates or ($C_1$-$C_4$)alkylarylsulfonates.

Among the quaternary ammonium salts of formula (X), preference is given, firstly, to tetraalkylammonium chlorides, for instance dialkyldimethylammonium or alkyltrimethylammonium chlorides in which the alkyl group includes from about 12 to 22 carbon atoms, in particular behenyltrimethylammonium chloride, distearyldimethylammonium chloride, cetyltrimethylammonium chloride or benzyldimethylstearylammonium chloride, or else, secondly, to distearoylethylhydroxyethylmethylammonium methosulfate, dipalmitoylethylhydroxyethylammonium methosulfate or distearoylethylhydroxyethylammonium methosulfate, or else, finally, to palmitylamidopropyltrimethylammonium chloride or stearamidopropyldimethyl(myristyl acetate)ammonium chloride, sold under the name Ceraphyl® 70 by the company Van Dyk.

quaternary ammonium salts of imidazoline, for instance those of formula (XI) below:

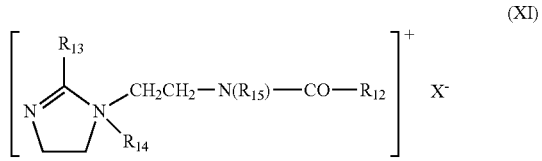

in which $R_{12}$ represents an alkenyl or alkyl group including from 8 to 30 carbon atoms, for example tallow fatty acid derivatives, $R_{13}$ represents a hydrogen atom, a $C_1$-$C_4$ alkyl group or an alkenyl or alkyl group including from 8 to 30 carbon atoms, $R_{14}$ represents a $C_1$-$C_4$ alkyl group, $R_{15}$ represents a hydrogen atom or a $C_1$-$C_4$ alkyl group, and $X^-$ is an anion chosen from the group of halides, phosphates, acetates, lactates, ($C_1$-$C_4$)alkyl sulfates and ($C_1$-$C_4$)alkylsulfonates or ($C_1$-$C_4$)alkylarylsulfonates.

Preferably, $R_{12}$ and $R_{13}$ denote a mixture of alkenyl or alkyl groups including from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo.

quaternary diammonium or triammonium salts, in particular of formula (XII) below:

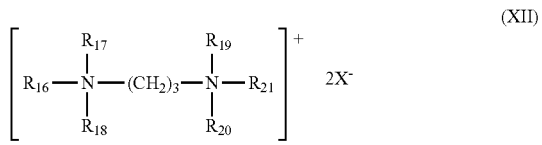

in which $R_{16}$ denotes an alkyl group containing approximately from 16 to 30 carbon atoms, which is optionally hydroxylated and/or interrupted with one or more oxygen atoms; $R_{17}$ is chosen from hydrogen, an alkyl group containing from 1 to 4 carbon atoms or a group —($CH_2$)$_3$—N$^+$(R16a)(R17a)(R18a), R16a, R17a, R18a, $R_{18}$, $R_{19}$, $R_{20}$ and $R_{21}$, which may be identical or different, are chosen from hydrogen or an alkyl group containing from 1 to 4 carbon atoms, and $X^-$ is an anion chosen from the group of halides, acetates, phosphates, nitrates, ($C_1$-$C_4$)alkyl sulfates, ($C_1$-$C_4$) alkylsulfonates or ($C_1$-$C_4$)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75).

quaternary ammonium salts containing one or more ester functions, for instance those of formula (XIII) below:

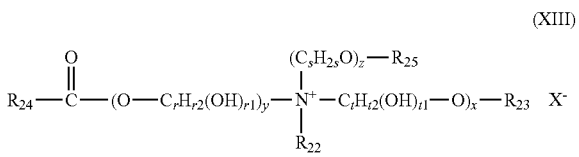

in which: $R_{22}$ is chosen from C1-$C_6$ alkyl groups and C1-C hydroxyalkyl or dihydroxyalkyl groups; $R_{23}$ is chosen from: the group —C(O)$R_{26}$, linear or branched, saturated or unsaturated C1-$C_{22}$ hydrocarbon-based groups $R_{27}$, or a hydrogen atom; $R_{25}$ is chosen from: the group —C(O)$R_{28}$, linear or branched, saturated or unsaturated C1-C hydrocarbon-based groups $R_{29}$, or a hydrogen atom; $R_{24}$, $R_{26}$ and $R_{28}$, which may be identical or different, are chosen from linear or branched, saturated or unsaturated $C_7$-$C_{21}$ hydrocarbon-based groups; r, s and t, which may be identical or different, are integers from 2 to 6; r1 and t1, which may be identical or different, are 0 or 1; r2+r1=2 r and t1+t2=2 t, y is an integer from 1 to 10, x and z, which may be identical or different, are integers from 0 to 10, $X^-$ is an organic or inorganic simple or complex anion, with the proviso that the sum x+y+z is from 1 to 15, that when x is 0 $R_{23}$ denotes $R_{27}$ and that when z is 0 $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a ($C_1$-$C_4$)alkyl sulfate, ($C_1$-$C_4$)alkylsulfonate or ($C_1$-$C_4$)alkylarylsulfonate. However, use may be made of methanesulfonate, phosphate, nitrate, tosylate, an anion derived from an organic acid, such as acetate or lactate, or any other anion that is compatible with the ammonium bearing an ester function.

The anion $X^-$ is even more particularly chloride, methyl sulfate or ethyl sulfate.

Use is made more particularly, in the composition according to the invention, of the ammonium salts of formula (XIII) in which: $R_{22}$ denotes a methyl or ethyl group, x and y are equal to 1, z is equal to 0 or 1, r, s and t are equal to 2; $R_{23}$ is chosen from: the group $—C(O)R_{26}$, methyl, ethyl or $C_{14}$-$C_{22}$ hydrocarbon-based groups, or a hydrogen atom, $R_{25}$ is chosen from: the group $—C(O)R_{28}$, or a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (XIII), examples that may be mentioned include the salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with mixtures of fatty acids of plant or animal origin, or by transesterification of the methyl esters thereof. This esterification is followed by quaternization by means of an alkylating agent, such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in U.S. Pat. Nos. 4,874,554 and 4,137,180.

Use may also be made of the behenoylhydroxypropyltrimethylammonium chloride sold, for example, by the company KAO under the name Quartamin BTC 131.

Preferably, the ammonium salts containing at least one ester function contain two ester functions.

Among the cationic surfactants, it is more particularly preferred to choose cetyltrimethylammonium, behenyltrimethylammonium and dipalmitoylethylhydroxyethyl-methylammonium salts, and mixtures thereof, and more particularly behenyl-trimethylammonium chloride, cetyltrimethylammonium chloride, and dipalmitoylethylhydroxyethylammonium methosulfate, and mixtures thereof.

Preferably, the surfactant(s) different from the alkyl(poly)glycosides is (are) chosen from anionic surfactants, non-ionic surfactants, and mixtures thereof.

More preferentially, the surfactant(s) different from the alkyl(poly)glycosides is (are) chosen from non-ionic surfactants, better still from ethoxylated $C_8$-$C_{24}$ fatty alcohols comprising from 1 to 200 ethylene oxide groups, ethoxylated C8-$C_{30}$ fatty acid esters of sorbitan having from 1 to 30 ethylene oxide units, and mixtures thereof.

When the composition comprises one or more surfactant(s) different from the alkyl(poly)glycosidesoxyethylenated $C_8$-$C_{30}$ fatty acid esters of sorbitan, the total content of surfactant(s) different from the alkyl(poly)glycosides in the composition preferably ranges from 0.01% to 20% by weight, more preferentially from 0.1% to 15% by weight, better still from 0.5% to 10% by weight, even better still from 1% to 8% by weight, relative to the total weight of the composition.

When the composition comprises one or more non-ionic surfactant(s) different from the alkyl(poly)glycosides, the total content of non-ionic surfactant(s) different from the alkyl(poly)glycosides in the composition preferably ranges from 0.01% to 20% by weight, more preferentially from 0.1% to 15% by weight, better still from 0.5% to 10% by weight, even better still from 1% to 8% by weight, relative to the total weight of the composition.

Sequestrant

The composition according to the invention may comprise a sequestrant (or chelating agent).

The definition of a "sequestrant" (or "chelating agent") is well known to those skilled in the art and refers to a compound or a mixture of compounds capable of forming a chelate with a metal ion. A chelate is an inorganic complex in which a compound (the sequestrant or chelating agent) is coordinated to a metal ion, i.e. it forms one or more bonds with the metal ion (formation of a ring including the metal ion).

A sequestrant (or chelating agent) generally comprises at least two electron-donating atoms which enable the formation of bonds with the metal ion.

Within the context of the present invention, the sequestrant(s) may be chosen from carboxylic acids, preferably aminocarboxylic acids, phosphonic acids, preferably aminophosphonic acids, polyphosphoric acids, preferably linear polyphosphoric acids, salts thereof, and derivatives thereof.

The salts are in particular alkali metal, alkaline-earth metal, ammonium and substituted ammonium salts.

The following compounds may be mentioned as examples of sequestrants based on carboxylic acids: diethylenetriaminepentaacetic acid (DTPA), ethylenediaminedisuccinic acid (EDDS) and trisodium ethylenediaminedisuccinate such as Octaquest E30 from OCTEL, ethylenediaminetetraacetic acid (EDTA), and its salts such as disodium EDTA, tetrasodium EDTA, ethylenediamine-N,N'-diglutaric acid (EDDG), glycinamide-N,N'-disuccinic acid (GADS), glycinamide-N,N'-disuccinic acid (GADS), 2-hydroxypropylenediamine-N,N'-disuccinic acid (HPDDS), ethylenediamine-N,N'-bis(ortho-hydroxyphenylacetic acid) (EDDHA), N,N'-bis(2-hydroxybenzyl)ethylenediamine-N,N'-diacetic acid (HBED), nitrilotriacetic acid (NTA), methylglycinediacetic acid (MGDA), N-2-hydroxyethyl-N,N-diacetic acid and glyceryliminodiacetic acid (as described in documents EP-A-317,542 and EP-A-399,133), iminodiacetic acid-N-2-hydroxypropylsulfonic acid and aspartic acid-N-carboxymethyl-N-2-hydroxypropyl-3-sulfonic acid (as described in EP-A-516,102), beta-alanine-N,N'-diacetic acid, aspartic acid-N,N'-diacetic acid, aspartic acid-N-monoacetic acid (described in EP-A-509,382), chelating agents based on iminodisuccinic acids (IDSA) (as described in EP-A-509, 382), ethanoldiglycine acid, phosphonobutanetricarboxylic acid such as the compound sold by Bayer under the reference Bayhibit AM, and N,N-dicarboxymethylglutamic acid and salts thereof such as tetrasodium glutamate diacetate (GLDA) such as Dissolvine GL38 or 45S from Akzo Nobel.

The following compounds may be mentioned as examples of chelating agents based on mono- or polyphosphonic acid: diethylenetriaminepenta(methylenephosphonic acid) (DTPMP), ethane-1-hydroxy-1,1,2-triphosphonic acid (E1HTP), ethane-2-hydroxy-1,1,2-triphosphonic acid (E2HTP), ethane-1-hydroxy-1,1-triphosphonic acid (EHDP), ethane-1,1,2-triphosphonic acid (ETP), ethylenediaminetetramethylenephosphonic acid (EDTMP), hydroxyethane-1,1-diphosphonic acid (HEDP, or etidronic acid), and salts such as disodium etidronate, tetrasodium etidronate.

The following compounds may be mentioned as examples of chelating agents based on polyphosphoric acid: sodium tripolyphosphate (STP), tetrasodium diphosphate, hexametaphosphoric acid, sodium metaphosphate, phytic acid.

According to a particular embodiment, the sequestrant(s) useful according to the invention is (are) phosphorus-based sequestrants, i.e. sequestrants which comprise one or more phosphorus atoms, preferably at least two phosphorus atoms.

The phosphorus-based sequestrant(s) used in the composition according to the invention is (are) preferably chosen from:
  inorganic phosphorus-based derivatives preferably chosen from alkali metal or alkaline-earth metal, preferably alkali metal, phosphates and pyrophosphates, such as sodium pyrophosphate, potassium pyrophosphate, sodium pyrophosphate decahydrate; and alkali metal or alkaline-earth metal, preferably alkali metal, polyphosphates, such as sodium hexametaphosphate, sodium polyphosphate, sodium tripolyphosphate, sodium trimetaphosphate; which are optionally hydrated, and mixtures thereof;
  organic phosphorus-based derivatives, such as organic (poly)phosphates and (poly)phosphonates, such as etidronic acid and/or alkali metal or alkaline-earth metal salts thereof, for instance tetrasodium etidronate, disodium etidronate, and mixtures thereof.

Preferably, the phosphorus-based sequestrant(s) is (are) chosen from linear or cyclic compounds comprising at least two phosphorus atoms bonded together covalently via at least one linker L comprising at least one oxygen atom and/or at least one carbon atom.

The phosphorus-based sequestrant(s) may be chosen from inorganic phosphorus-based derivatives, preferably comprising at least 2 phosphorus atoms. More preferentially, the phosphorus-based sequestrant(s) is (are) chosen from alkali metal or alkaline-earth metal pyrophosphates, better still from alkali metal pyrophosphates, in particular sodium pyrophosphate (also known as tetrasodium pyrophosphate).

The phosphorus-based sequestrant(s) may be chosen from organic phosphorus-based derivatives, preferably comprising at least 2 phosphorus atoms. More preferentially, the phosphorus-based sequestrant(s) is (are) chosen from etidronic acid (also known as 1-hydroxyethane-1,1-diphosphonic acid) and/or alkali metal or alkaline-earth metal, preferably alkali metal, salts thereof, for instance tetrasodium etidronate and disodium etidronate.

Thus, preferably, the phosphorus-based sequestrant(s) is (are) chosen from alkali metal pyrophosphates, etidronic acid and/or alkali metal salts thereof, and a mixture of these compounds.

Particularly preferably, the phosphorus-based sequestrant(s) is (are) chosen from tetrasodium etidronate, disodium etidronate, etidronic acid, tetrasodium pyrophosphate, and a mixture of these compounds.

According to the present invention, the sequestrants are preferably chosen from diethylenetriaminepentaacetic acid (DTPA) and salts thereof, diethylenediaminetetraacetic acid (EDTA) and salts thereof, ethylenediaminedisuccinic acid (EDDS) and salts thereof, etidronic acid and salts thereof, N,N-dicarboxymethylglutamic acid and salts thereof, N,N-dicarboxymethylglutamic acid and salts thereof (GLDA), and mixtures thereof.

Among the salts of these compounds, the alkali metal salts and especially the sodium or potassium salts are preferred.

When the composition comprises one or more sequestrants, the total content of the sequestrant(s) preferably ranges from 0.001% to 15% by weight, more preferentially from 0.005% to 10% by weight, better still from 0.01% to 8% by weight, even better still from 0.05% to 5% by weight, relative to the total weight of the composition.

Thickening Polymer

The composition according to the present invention may comprise one or more thickening polymer(s).

For the purposes of the invention, the term "thickening" is understood to mean a compound capable, by its presence, of increasing the viscosity of the medium by at least 50 cps at 25° C. and at a shear rate of 1 $s^{-1}$. Preferably, the thickening compound, introduced at 1% by weight in water or in a 50/50 water/alcohol mixture, achieves a viscosity at 25° C. of greater than 100 cps at a shear rate of 1 $s^{-1}$. These viscosities can be measured using in particular viscometers or rheometers having cone-plate geometry.

The thickening polymers can be chosen from associative polymers and non-associative polymers.

For the purposes of the present invention, the term "associative polymers" means water-soluble polymers that are capable, in an aqueous medium, of reversibly associating with each other or with other molecules.

Their chemical structure comprises at least one hydrophilic region and at least one hydrophobic region characterized by at least one $C_8$-$C_{30}$ fatty chain.

The associative polymers according to the invention may be of anionic, cationic, amphoteric or non-ionic type, preferably of non-ionic or cationic type.

Mention may in particular be made of the polymers sold under the names Pemulen TR1 or TR2 by the company Goodrich (INCI: Acrylates/C10-30 Alkyl Acrylate Crosspolymer), Salcare SC90 by the company Ciba, Aculyn 22, 28, 33, 44 or 46 by the company Röhm & Haas and Elfacos T210 and T212 by the company Akzo.

Preferably, the associative polymers can be chosen from cellulose-based polymers.

Preferably, the associative polymer(s) is (are) chosen from celluloses modified with groups comprising at least one fatty chain.

Preferentially, the associative polymer(s) may be chosen from hydroxyethylcelluloses modified with groups including at least one fatty chain, such as alkyl, arylalkyl or alkylaryl groups, or mixtures thereof, and in which the alkyl groups are preferably $C_8$-$C_{22}$, and hydroxyethylcelluloses modified with polyalkylene glycol alkyl phenol ether groups, and mixtures thereof, preferably cetylhydroxyethylcellulose.

Preferentially, the associative polymer(s) may be chosen from quaternized cellulose derivatives, preferably chosen from quaternized hydroxyethylcelluloses modified with groups comprising at least one fatty chain, such as linear or branched alkyl groups, linear or branched arylalkyl groups, or linear or branched alkylaryl groups, preferably linear or branched alkyl groups, these groups comprising at least 8 carbon atoms, notably from 8 to 30 carbon atoms, better still from 10 to 24, or even from 10 to 14, carbon atoms; or mixtures thereof, and even better still polyquaternium-67.

The thickening polymers may also be chosen from non-associative polymers, and in particular non-ionic cellulose-based polymers (hydroxyethycellulose, hydroxypropylcellulose, carboxymethylcellulose), guar gum and non-ionic derivatives thereof (hydroxypropylguar), gums of microbial origin (xanthan gum, scleroglucan gum), crosslinked or non-crosslinked homopolymers and copolymers based on acrylic acid, on methacrylic acid or on acrylamidopropanesulfonic acid, and mixtures thereof.

Among the non-associative polymers, an anionic (meth) acrylic polymer may also be chosen, such as homopolymers or copolymers of (meth)acrylic acid. Mention may for example be made of the compounds having the INCI name Carbomer.

Preferably, the non-associative polymers are chosen from guar gums, xanthan gum, and homopolymers or copolymers of (meth)acrylic acid.

The guar gums that may be used according to the invention may be non-ionic or cationic.

According to the invention, use may be made of chemically modified or unmodified non-ionic guar gums.

The unmodified non-ionic guar gums are, for example, the products sold under the name Vidogum GH 175 by the company Unipectine and under the names Meypro-Guar 50 and Jaguar C by the company Rhodia Chimie.

The modified non-ionic guar gums that may be used according to the invention are preferably modified with C1-C6 hydroxyalkyl groups.

Among the hydroxyalkyl groups, mention may be made, by way of example, of hydroxymethyl, hydroxyethyl, hydroxypropyl and hydroxybutyl groups.

These guar gums are well known from the prior art and may be prepared, for example, by reacting corresponding alkene oxides, for instance propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such non-ionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall, or under the name Galactasol 4H4FD2 by the company Aqualon.

Also suitable for use are non-ionic guar gums modified with hydroxyalkyl groups, more especially hydroxypropyl groups, modified with groups comprising at least one $C_6$-$C_{30}$ fatty chain. Examples of such compounds that may be mentioned include, inter alia, the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhone-Poulenc.

The cationic guar gums that may more particularly be used according to the invention are guar gums comprising trialkylammonium cationic groups. Preferably, 2% to 30% and more preferentially still 5% to 20% by number of the hydroxyl functions of these guar gums bear trialkylammonium cationic groups.

Among these trialkylammonium groups, mention may most particularly be made of the trimethylammonium and triethylammonium groups.

Even more preferentially, these groups represent from 5% to 20% by weight relative to the total weight of the modified guar gum.

According to the invention, a guar gum modified with 2,3-epoxypropyltrimethylammonium chloride is preferably used.

These guar gums modified with cationic groups are products already known per se and are, for example, described in patents U.S. Pat. Nos. 3,589,578 and 4,013,307. Such products are moreover notably sold under the trade names Jaguar C13 S, Jaguar C 15 and Jaguar C 17 by the company Meyhall.

Use is preferably made of a non-ionic guar gum and, among these non-ionic guar gums, more particularly guar gums modified with hydroxyalkyl groups.

When the composition comprises one or more thickening polymers, the total content of the thickening polymer(s) preferably ranges from 0.01% to 20% by weight, more preferentially from 0.05% to 10% by weight, better still from 0.075% to 5% by weight, even better still from 0.1% to 3% by weight, relative to the total weight of the composition.

Alkaline Agent

The composition according to the present invention may comprise one or more mineral, organic or hybrid alkaline agent(s).

Preferably, the composition according to the present invention comprises one or more mineral, organic or hybrid alkaline agent(s).

For the purposes of the present invention, the terms "alkaline agent" and "basifying agent" are used interchangeably.

The mineral basifying agent(s) is (are) preferably chosen from aqueous ammonia, alkali metal carbonates or bicarbonates such as sodium (hydrogen)carbonate and potassium (hydrogen)carbonate, alkali metal or alkaline-earth metal phosphates such as sodium phosphates or potassium phosphates, sodium or potassium hydroxides, and mixtures thereof.

The organic basifying agent(s) is (are) preferably chosen from alkanolamines, amino acids, organic amines, oxyethylenated and/or oxypropylenated ethylenediamines, 1,3-diaminopropane, 1,3-diamino-2-propanol, spermine or spermidine and mixtures thereof.

The term "alkanolamine" is intended to mean an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for carrying out the invention.

In particular, the alkanolamine(s) is (are) chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane and mixtures thereof.

Advantageously, the amino acids are basic amino acids comprising an additional amine function. Such basic amino acids are preferably chosen from histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole. The organic amine may also be chosen from amino acid dipeptides. As amino acid dipeptides that may be used in the present invention, mention may notably be made of carnosine, anserine and balenine. The organic amine may also be chosen from compounds comprising a guanidine function. As amines of this type other than arginine that may be used in the present invention, mention may especially be made of creatine, creatinine, 1,1-dimethylguanidine, 1,1-diethylguanidine, glycocyamine, metformin, agmatine, n-amidoalanine, 3-guanidinopropionic acid, 4-guanidinobutyric acid and 2-([amino(imino)methyl]amino)ethane-1-sulfonic acid.

Use may be made in particular of guanidine carbonate or monoethanolamine hydrochloride as hybrid compounds.

The alkaline agent(s) that may be used according to the invention is (are) preferably chosen from alkanolamines such as monoethanolamine, diethanolamine, triethanolamine; aqueous ammonia, carbonates or bicarbonates such as sodium (hydrogen)carbonate and potassium (hydrogen)carbonate and mixtures thereof, more preferentially from aqueous ammonia and alkanolamines, better still from alkanolamines.

When the composition comprises at least one alkaline agent, the total content of the alkaline agent(s) preferably ranges from 0.1% to 40% by weight, more preferentially from 0.5% to 30% by weight, better still from 1% to 20% by weight, even better still from 2% to 10% by weight, relative to the total weight of the composition.

According to an embodiment, the pH of the composition comprising at least one alkaline agent, when it is aqueous, is between 8 and 13; preferably between 9 and 12.

The pH of the composition may be adjusted to the desired value by means of acidic or alkaline agent(s) commonly used in the dyeing of keratin fibres, such as those described hereinabove, or alternatively using buffer systems known to those skilled in the art.

Solvents

The composition according to the invention may also comprise at least one organic solvent.

Examples of organic solvents that may be mentioned include linear or branched $C_2$ to C4 alkanols, such as ethanol and isopropanol; polyols and polyol ethers, for instance 2-butoxyethanol, glycerol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The organic solvent(s) may be present in an amount ranging from 0.01% to 30% by weight, preferably ranging from 2% to 25% by weight, relative to the total weight of the composition.

In addition, the composition according to the invention is preferably an aqueous composition. The composition preferably comprises water in an amount of greater than or equal to 5% by weight, preferably greater than or equal to 10% by weight, better still greater than or equal to 15% by weight, relative to the total weight of the composition.

Additives

The composition according to the invention may optionally comprise one or more additives, different from the compounds of the invention and among which mention may be made of cationic, anionic, non-ionic or amphoteric polymers or mixtures thereof, other than thickening polymers, mineral thickening agents, antidandruff agents, anti-seborrhoeic agents, agents for preventing hair loss and/or for promoting hair regrowth, vitamins and provitamins including panthenol, sunscreens, mineral or organic pigments, plasticizers, solubilizers, opacifiers or pearlescent agents, antioxidants, hydroxy acids, fragrances, and preservatives.

Of course, those skilled in the art will take care to choose this or these optional additional compound(s) so that the advantageous properties intrinsically associated with the composition according to the invention are not, or not substantially, detrimentally affected by the envisioned addition(s).

The above additives may generally be present in an amount, for each of them, of between 0 and 20% by weight, relative to the total weight of the composition.

Preferably, the composition according to the invention does not comprise chemical oxidizing agents.

According to a particular embodiment, the composition according to the invention comprises:
  at least one oxidation coupler chosen from hydroxyethyl-3,4-methylenedioxyaniline of formula (I), one of its addition salts, its solvates and/or the solvates of its salts,

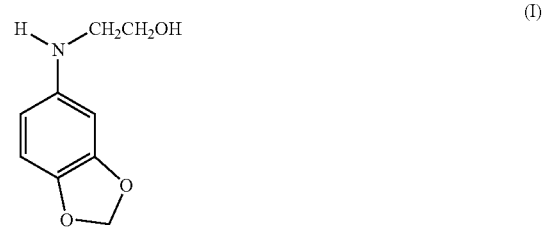

at least one oxidation coupler chosen from 2-amino-5-ethylphenol of formula (II), one of its addition salts, its solvates and/or the solvates of its salts,

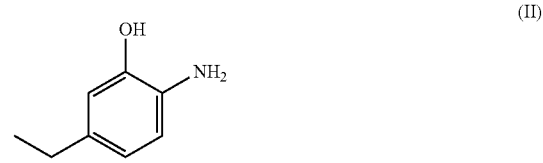

at least one alkyl(poly)glycoside,
  at least one fatty substance,
  at least one surfactant, preferably non-ionic, different from the alkyl(poly)glycosides,
  at least one sequestrant, and
  at least one alkaline agent.

Process

The present invention also relates to a process for dyeing keratin fibres, preferably the hair, which comprises the step of applying to said keratin fibres an effective amount of a composition as described above.

The composition may be applied to wet or dry keratin fibres. On conclusion of the treatment, the keratin fibres are optionally rinsed with water, optionally washed with a shampoo and then rinsed with water, before being dried or left to dry.

Preferably, the process according to the invention comprises a step of mixing the composition according to the invention with an oxidizing composition comprising at least one chemical oxidizing agent. This mixing step is preferably performed at the moment of use, just before applying the composition resulting from the mixing to the hair.

More particularly, the chemical oxidizing agent(s) is (are) chosen from hydrogen peroxide, urea peroxide, alkali metal bromates or ferricyanides, peroxygenated salts, for instance persulfates, perborates, peracids and precursors thereof and percarbonates of alkali metals or alkaline-earth metals, and mixtures thereof. The oxidizing agent is preferably chosen from hydrogen peroxide.

The oxidizing composition is preferably an aqueous composition. In particular, it comprises more than 5% by weight of water, preferably more than 10% by weight of water, and even more advantageously more than 20% by weight of water.

It may also comprise one or more organic solvents chosen from those listed previously; these solvents more particularly representing, when they are present, from 1% to 40% by weight and preferably from 5% to 30% by weight, relative to the weight of the oxidizing composition.

The oxidizing composition also preferably comprises one or more acidifying agents. Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

The oxidizing composition may additionally comprise fatty substances such as those described hereinabove, preferably chosen from fatty alcohols, liquid hydrocarbons comprising more than 16 carbon atoms and mixtures thereof, surfactants and polymers.

Usually, the pH of the oxidizing composition, when it is aqueous, is less than 7.

Preferably, the oxidizing composition comprises hydrogen peroxide as oxidizing agent, in aqueous solution, the concentration of which ranges, more particularly, from 0.1% to 50%, more particularly between 0.5% and 20% and even more preferentially between 1% and 15% by weight, relative to the weight of the oxidizing composition.

Preferably, at least one of the (dye or oxidizing) compositions is aqueous.

Preferably, the process according to the invention comprises a step of applying to the hair a composition resulting from the mixing, at the time of use, of at least two compositions:

a) a dyeing composition comprising:
at least one oxidation coupler chosen from hydroxyethyl-3,4-methylenedioxyaniline of formula (I), one of its addition salts, its solvates and/or the solvates of its salts,

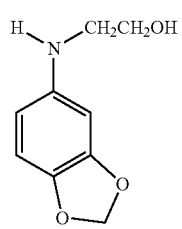

(I)

at least one oxidation coupler chosen from 2-amino-5-ethylphenol of formula (II), one of its addition salts, its solvates and/or the solvates of its salts,

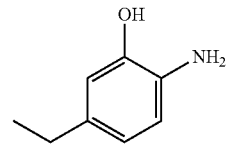

(II)

at least one alkyl(poly)glycoside,
and
b) an oxidizing composition comprising one or more chemical oxidizing agents, preferably hydrogen peroxide.

According to one particular embodiment, the process according to the invention comprises a step of applying to the hair a composition resulting from the mixing, at the time of use, of at least two compositions:

a) a dyeing composition comprising:
at least one oxidation coupler chosen from hydroxyethyl-3,4-methylenedioxyaniline of formula (I), one of its addition salts, its solvates and/or the solvates of its salts,

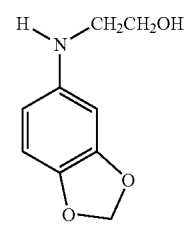

(I)

at least one oxidation coupler chosen from 2-amino-5-ethylphenol of formula (II), one of its addition salts, its solvates and/or the solvates of its salts,

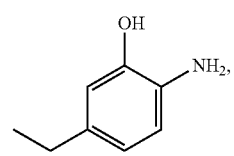

(II)

at least one alkyl(poly)glycoside,
at least one fatty substance,
at least one surfactant, preferably non-ionic, different from the alkyl(poly)glycosides,
at least one sequestrant, and
at least one alkaline agent,
and
b) an oxidizing composition comprising one or more chemical oxidizing agents, preferably hydrogen peroxide.

The invention also relates to a composition comprising:
at least one oxidation coupler chosen from hydroxyethyl-3,4-methylenedioxyaniline of formula (I), one of its addition salts, its solvates and/or the solvates of its salts,

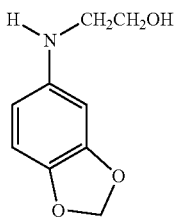

at least one oxidation coupler chosen from 2-amino-5-ethylphenol of formula (II), one of its addition salts, its solvates and/or the solvates of its salts,

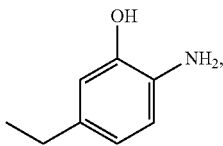

at least one alkyl(poly)glycoside, and one or more chemical oxidizing agents, preferably hydrogen peroxide, this composition being a ready-to-use composition.

This ready-to-use composition may comprise one or more ingredients among those described above.

Preferably, the pH of the ready-to-use composition is between 8 and 11, preferably between 9 and 10.7.

Kit

Another subject of the invention is a multi-compartment device for dyeing keratin fibres, comprising at least a first compartment containing the dyeing composition according to the invention and at least a second compartment containing an oxidizing composition as described above.

The compositions of the device according to the invention are packaged in separate compartments, optionally accompanied by suitable application means which may be identical or different, such as fine brushes, coarse brushes or sponges.

The device mentioned above may also be equipped with a means for dispensing the desired mixture onto the hair, for instance the devices described in patent FR 2586913.

Finally, the present invention relates to the use of a composition as described above for dyeing keratin fibres, and in particular the hair.

The following examples serve to illustrate the invention without, however, being limiting in nature.

EXAMPLES

In the examples that follow, all the amounts are given as weight percentage of active material (AM) relative to the total weight of the composition (unless stated otherwise).

Dyeing Composition

Composition A1 according to the present invention and comparative compositions A2 and A3 were prepared using the ingredients of which the contents are indicated in the table below:

TABLE 1

|  | A1 (invention) | A2 (comparative) | A3 (comparative) |
| --- | --- | --- | --- |
| 2-AMINO-5-ETHYLPHENOL HCL | 2.1 mmol | — | 4.2 mmol |
| HYDROXYETHYL-3,4-METHYLENEDIOXYANILINE HCL | 2.1 mmol | 4.2 mmol | — |
| m-AMINOPHENOL | 0.31 | 0.31 | 0.31 |
| 6-HYDROXYINDOLE | 0.052 | 0.052 | 0.052 |
| 2-AMINO-3-HYDROXYPYRIDINE | 0.04 | 0.04 | 0.04 |
| N,N-BIS(2-HYDROXYETHYL)-p-PHENYLENEDIAMINE SULFATE | 0.06 | 0.06 | 0.06 |
| TOLUENE-2,5 DIAMINE | 0.9 | 0.9 | 0.9 |
| 2,4-DIAMINOPHENOXYETHANOL HCL | 0.09 | 0.09 | 0.09 |
| MONOETHANOLAMINE | 4.95 | 4.95 | 4.95 |
| SODIUM METABISULFITE | 0.45 | 0.45 | 0.45 |
| MINERAL OIL | 59.7 | 59.7 | 59.7 |
| *LIMNANTHES ALBA* (MEADOWFOAM) SEED OIL | 0.1 | 0.1 | 0.1 |
| *HELIANTHUS ANNUUS* (SUNFLOWER) SEED OIL | 0.1 | 0.1 | 0.1 |
| PASSIFLORA INCARNATA SEED OIL | 0.1 | 0.1 | 0.1 |
| CAMELLIA OLEIFERA SEED OIL | 0.1 | 0.1 | 0.1 |
| CAPRYLYL/CAPRYL GLUCOSIDE | 2.4 | 2.4 | 2.4 |
| POLYSORBATE 21 | 2.4 | 2.4 | 2.4 |
| STEARETH-20 | 3.88 | 3.88 | 3.88 |
| STEARETH-2 | 1.13 | 1.13 | 1.13 |
| POLYQUATERNIUM-67 | 0.2 | 0.2 | 0.2 |
| EDTA | 0.2 | 0.2 | 0.2 |
| ASCORBIC ACID | 0.25 | 0.25 | 0.25 |
| perfume | qs | qs | qs |
| water | qs 100 | qs 100 | qs 100 |

Oxidizing Composition

The oxidizing composition B was prepared from the ingredients of which the contents are indicated in the table below:

TABLE 2

| Ingredients | B |
| --- | --- |
| SODIUM SALICYLATE | 0.035 |
| TETRASODIUM PYROPHOSPHATE | 0.04 |
| HYDROGEN PEROXIDE | 6 |

TABLE 2-continued

| Ingredients | B |
| --- | --- |
| CETEARYL ALCOHOL | 2.28 |
| CETEARETH-25 | 0.57 |
| TETRASODIUM ETIDRONATE | 0.06 |
| TRIDECETH-2 CARBOXAMIDE MEA | 0.85 |
| GLYCEROL | 0.5 |
| PHOSPHORIC ACID | qs pH 2.2 |
| Water | qs 100 |

Dyeing Protocol

The dyeing compositions A1, A2 and A3 are each mixed with the oxidizing composition B in a 1+1 weight ratio.

Each of the mixtures is applied to locks of hair containing 90% natural white (NW) hair and 90% permanent-waved natural white (PW) hair, in a proportion of 5 g of mixture per 1 g of hair.

After a leave-on time of 30 minutes on a hot plate at 27° C., the hair is rinsed, washed with L'Oréal Professionnel Pro Classic universal concentrated shampoo, diluted to 10%, and dried.

Results

The colouring of the hair is evaluated in the $L^*a^*b^*$ system, using a Konica Minolta CM-3600A spectrocolorimeter (illuminant D65, angle 10°, specular component included) in the CIELab system.

In this system, $L^*$ represents the lightness. The lower the value of $L^*$, the darker and more powerful the colouring obtained. The chromaticity is measured by the values $a^*$ and $b^*$, $a^*$ representing the red/green axis and $b^*$ the yellow/blue axis.

The selectivity is represented by the colour difference $\Delta E$ between the locks of dyed natural (NW) hair and dyed permanent-waved (PW) hair, $\Delta E$ being obtained from the formula:

$$\Delta E = \sqrt{(L^*-L_0^*)^2+(a^*-a_0^*)^2+(b^*-b_0^*)^2}$$

in which $L^*$ represents the intensity and $a^*$ and $b^*$ represent the chromaticity of the dyed natural hair, and $L_0^*$ represents the intensity and $a_0^*$ and $b_0^*$ represent the chromaticity of the dyed permanent-waved hair. The lower the value of $\Delta E$, the lower the selectivity and the more uniform the colouration along the hair.

TABLE 3

|  | $\Delta E$ |
| --- | --- |
| A1 + B (invention) | 0.53 |
| A2 + B (comparative) | 2.70 |
| A3 + B (comparative) | 2.69 |

The composition according to the invention A1 leads to a lower value of $\Delta E$, and thus to better selectivity, compared to the comparative compositions A2 and A3.

The invention claimed is:

1. A composition comprising:
   i) at least one oxidation coupler chosen from hydroxyethyl-3,4-methylenedioxyaniline of formula (I), addition salts thereof, solvates thereof, solvates of its salts thereof, or mixtures of two or more thereof

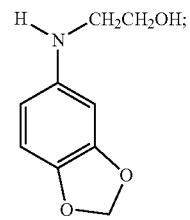
(I)

ii) at least one oxidation coupler chosen from 2-amino-5-ethylphenol of formula (II), addition salts thereof, solvates thereof, solvates of its salts thereof, or mixtures of two or more thereof

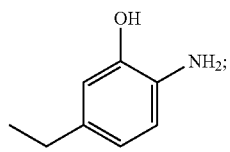
(II)

and
   iii) at least one alkyl(poly)glycoside.

2. The composition of claim 1, wherein the total amount of oxidation coupler(s) chosen from hydroxyethyl-3,4-methylenedioxyaniline(s) of formula (I), addition salts thereof, solvates thereof, solvates of its salts thereof, or mixtures of two or more ranges from 0.001% to 20% by weight, relative to the total weight of the composition.

3. The composition of claim 1, wherein the total amount of oxidation coupler(s) chosen from 2-amino-5-ethylphenol(s) of formula (II), addition salts thereof, solvates thereof, solvates of its salts thereof, or mixtures of two or more thereof ranges from 0.001% to 20% by weight, relative to the total weight of the composition.

4. The composition of claim 1, further comprising at least one oxidation base.

5. The composition of claim 4, wherein the at least one oxidation base is chosen from para-phenylenediamines, bis(phenyl)alkylenediamines, para-aminophenols, ortho-aminophenols, heterocyclic bases, addition salts thereof, or mixtures of two or more thereof.

6. The composition of claim 4, wherein the total amount of oxidation base(s) ranges from 0.001% to 20% by weight, relative to the weight of the composition.

7. The composition of claim 4, wherein the weight ratio of the total amount of oxidation base(s) to the total amount of oxidation coupler(s) chosen from i) hydroxyethyl-3,4-methylenedioxyaniline(s) of formula (I), addition salts thereof, solvates thereof, solvates of their salts thereof, or mixtures of two or more thereof, ii) 2-amino-5-ethylphenol(s) of formula (II), addition salts thereof, solvates thereof, solvates of their salts thereof, or mixtures of two or more thereof, or iii) mixtures thereof ranges from 0.1:1 to 10:1.

8. The composition of claim 1, comprising at least one alkyl(poly)glycoside of formula $R_1O-(R_2O)t-(G)v$, wherein:
   $R_1$ represents a linear or branched alkyl or alkenyl radical comprising 6 to 24 carbon atoms, or an alkylphenyl radical comprising a linear or branched alkyl radical comprising 6 to 24 carbon atoms;
   $R_2$ represents an alkylene radical comprising from 2 to 4 carbon atoms, G represents a sugar unit comprising from 5 to 6 carbon atoms, t represents a number ranging from 0 to 10;

v represents a number ranging from 1 to 15.

9. The composition of claim 8, comprising at least one alkyl(poly)glycoside of formula $R_1O$-$(R_2O)t$-$(G)v$, wherein:
R$_1$ represents a saturated or unsaturated linear or branched alkyl radical comprising from 8 to 18 carbon atoms,
R$_2$ represents an alkylene radical comprising from 2 to 4 carbon atoms,
t represents a value ranging from 0 to 3,
G is chosen from glucose, fructose or galactose;
v represents a degree of polymerization ranging from 1 to 15.

10. The composition of claim 1, wherein the total amount of alkyl(poly)glycoside ranges from 0.05% to 20% by weight, relative to the total weight of the composition.

11. The composition of claim 1, further comprising at least one fatty substance.

12. The composition of claim 11, wherein the at least one fatty substance is chosen from at least one liquid fatty substance chosen from liquid hydrocarbons comprising more than 16 carbon atoms, plant oils, liquid fatty alcohols, liquid fatty esters, silicone oils, or mixtures of two or more thereof.

13. The composition of claim 11, wherein the at least one fatty substance is chosen from at least one solid fatty substance chosen from solid fatty acids, solid fatty alcohols, solid esters of fatty acids and/or of fatty alcohols, waxes, ceramides, or mixtures of two or more thereof.

14. The composition of claim 1, further comprising at least one surfactant1 different from the at least one alkyl (poly)glycoside.

15. The composition of claim 14, wherein the at least one surfactant different from the at least one alkyl(poly)glycoside is chosen from anionic surfactants, non-ionic surfactants, or mixtures thereof.

16. The composition of claim 1, further comprising at least one sequestrant.

17. The composition of claim 1, further comprising at least one alkaline agent chosen from alkanolamines, aqueous ammonia, carbonates, bicarbonates, or mixtures of two or more thereof.

18. The composition of claim 1, further comprising at least one chemical oxidizing agent.

19. A method for dyeing keratin fibers comprising:
a) mixing a dye composition (A) with an oxidizing composition (B),
wherein the dye composition (A) comprises:
i) at least one oxidation coupler chosen from hydroxyethyl-3,4-methylenedioxyaniline of formula (I), addition salts thereof, solvates thereof, solvates of its salts thereof, or mixtures of two or more thereof:

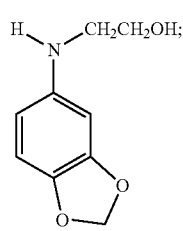

(I)

ii) at least one oxidation coupler chosen from 2-amino-5-ethylphenol of formula (II), addition salts thereof, solvates thereof, solvates of its salts thereof, or mixtures of two or more thereof:

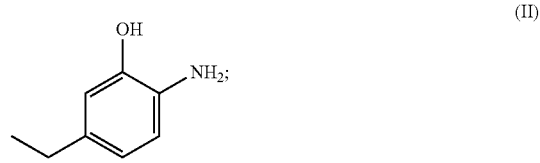

(II)

iii) at least one alkyl(poly)glycoside, and wherein the oxidizing composition (B) comprises at least one chemical oxidizing agent, and b) applying the mixture to keratin fibers.

20. A kit comprising a first container and a second container, wherein the first container comprises a dye composition (A) comprising:
i) at least one oxidation coupler chosen from hydroxyethyl-3,4-methylenedioxyaniline of formula (I), addition salts thereof, solvates thereof, solvates of its salts thereof, or mixtures of two or more thereof:

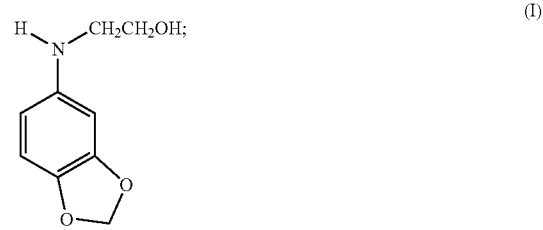

(I)

ii) at least one oxidation coupler chosen from 2-amino-5-ethylphenol of formula (II), addition salts thereof, solvates thereof, solvates of its salts thereof, or mixtures of two or more thereof:

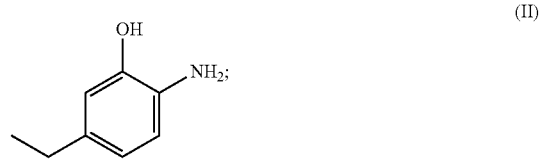

(II)

iii) at least one alkyl(poly)glycoside, and wherein the second container comprises an oxidizing composition (B) comprising at least one chemical oxidizing agent.

* * * * *

UNITED STATES PATENT AND TRADEMARK OFFICE
CERTIFICATE OF CORRECTION

PATENT NO. : 12,178,899 B2
APPLICATION NO. : 18/266725
DATED : December 31, 2024
INVENTOR(S) : Valérie Nicou et al.

Page 1 of 1

It is certified that error appears in the above-identified patent and that said Letters Patent is hereby corrected as shown below:

In the Claims

Claim 14, Column 37, Line 30, change "surfactantl" to -- surfactant --.

Signed and Sealed this
Twenty-fifth Day of March, 2025

Coke Morgan Stewart
*Acting Director of the United States Patent and Trademark Office*